United States Patent
Kaufmann

(10) Patent No.: US 6,809,825 B2
(45) Date of Patent: Oct. 26, 2004

(54) GAS PERMEABLE PROBE FOR USE IN AN OPTICAL ANALYZER FOR AN EXHAUST GAS STREAM FLOWING THROUGH A DUCT OR CHIMNEY

(75) Inventor: Jürgen Kaufmann, Waldkirch (DE)

(73) Assignee: Sick AG, Waldkirch (DE)

( * ) Notice: Subject to any disclaimer, the term of this patent is extended or adjusted under 35 U.S.C. 154(b) by 282 days.

(21) Appl. No.: 10/054,116

(22) Filed: Nov. 13, 2001

(65) Prior Publication Data

US 2003/0090665 A1 May 15, 2003

(51) Int. Cl.$^7$ ............................................. G01N 21/61
(52) U.S. Cl. ....................................................... 356/439
(58) Field of Search ................................ 356/437–439; 250/338.5, 343, 573

(56) References Cited

U.S. PATENT DOCUMENTS

| | | | |
|---|---|---|---|
| 4,549,080 A | * 10/1985 | Baskins et al. ............. | 250/343 |
| 4,560,873 A | 12/1985 | McGowan et al. | |
| 4,684,805 A | * 8/1987 | Shu-Ti Lee et al. ........ | 250/343 |
| 4,749,276 A | * 6/1988 | Bragg et al. ................ | 356/246 |
| 4,914,297 A | * 4/1990 | Wieboldt et al. ........... | 250/343 |
| 6,064,488 A | 5/2000 | Brand et al. | |

\* cited by examiner

Primary Examiner—Richard A. Rosenberger
(74) Attorney, Agent, or Firm—Townsend and Townsend and Crew LLP

(57) ABSTRACT

A gas permeable probe for use in an optical analyzer for an exhaust gas stream flowing through a duct or chimney has:

an elongate hollow structure having first and second ends and a side wall, with an optical cavity defined between the first and second ends within the side wall, a mounting structure at the first end and adapted for mounting the elongate hollow structure within the duct or chimney, a support member at the second end, a connecting structure connecting the mounting structure at the first end to the support member at the second end, an optical window at the first end permitting a beam of light originating from an optical analyzer to enter into the optical cavity to travel from the first end to the second end, a filter forming a part of the side wall, and a retroreflector provided at the second end for returning the light beam to the first end of the hollow structure, the optical window being releasably mounted at the first end of the elongate hollow structure and/or the retroreflector being releasably mounted at the second end of the elongate hollow structure.

33 Claims, 8 Drawing Sheets

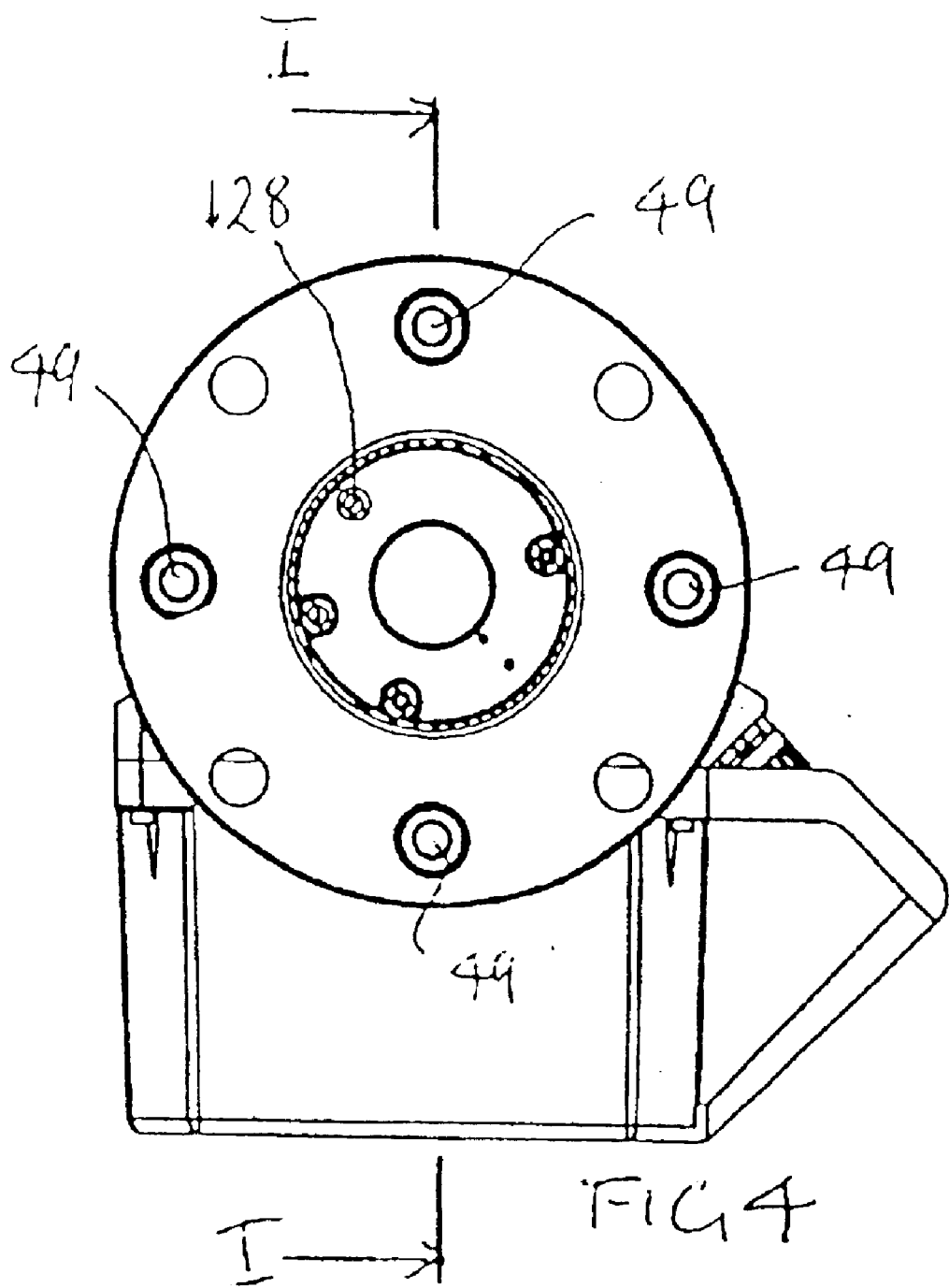

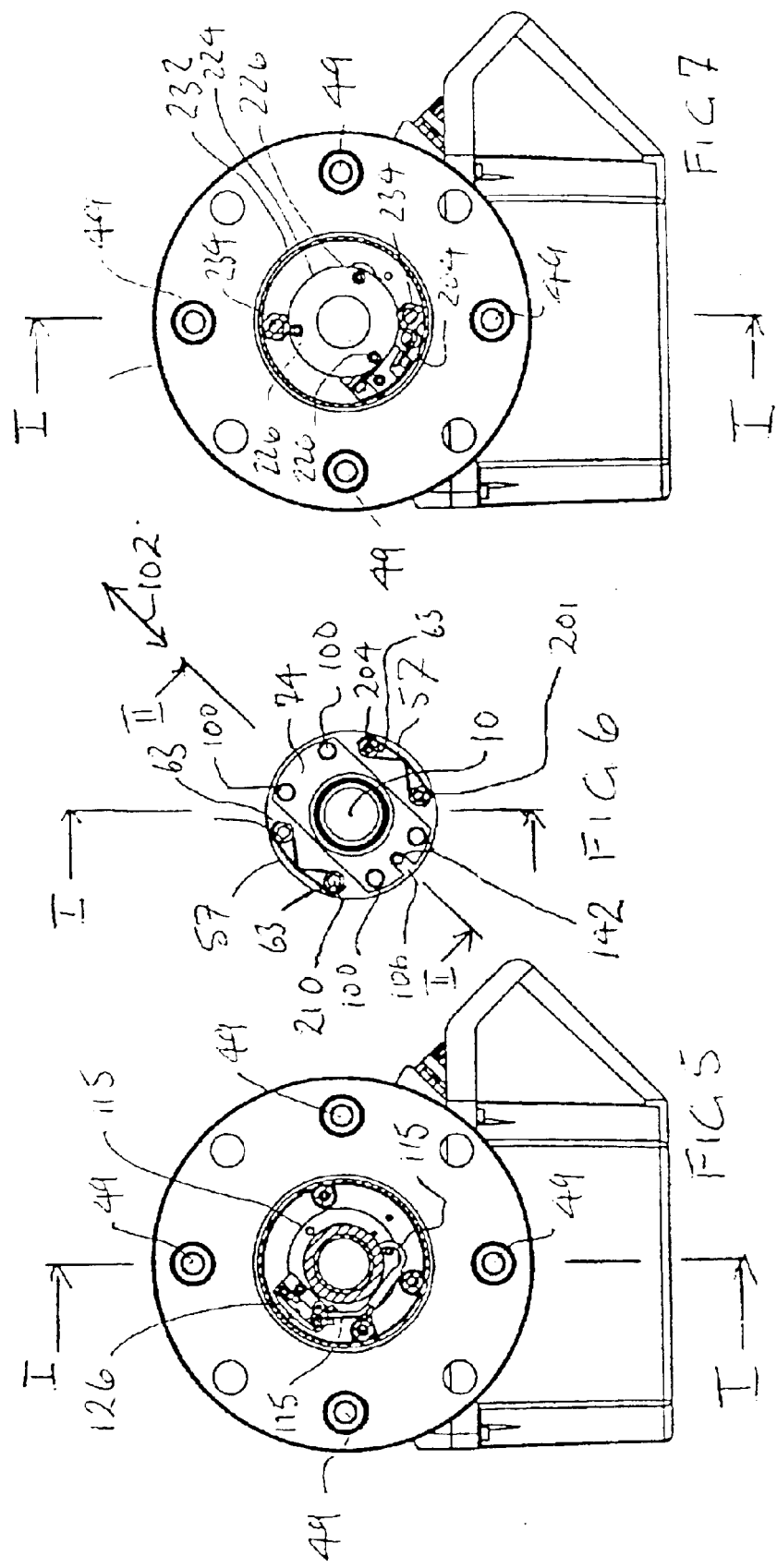

GAS PERMEABLE PROBE FOR USE IN AN OPTICAL ANALYZER FOR AN EXHAUST GAS STREAM FLOWING THROUGH A DUCT OR CHIMNEY

BACKGROUND OF THE INVENTION

The present invention relates to a gas permeable probe for use in an optical analyzer for an exhaust gas stream flowing through a duct or chimney, the probe comprising:

an elongate hollow structure having first and second ends and a side wall, with an optical cavity defined between the first and second ends within the side wall, a mounting structure at the first end and adapted for mounting the elongate hollow structure within the duct or chimney, a support member at the second end, a connecting structure connecting the mounting structure at the first end to the support member at the second end, an optical window at the first end permitting a beam of light originating from an optical analyzer to enter into the optical cavity to travel from the first end to the second end, a filter forming a part of the side wall, and a retroreflector provided at the second end for returning the light beam to the first end of the hollow structure.

A gas permeable probe of this kind is known, for example, from U.S. Pat. No. 4,560,873. The gas permeable probe disclosed in this reference utilizes a cylindrical ceramic filter to permit gas flowing through the chimney to enter into the optical cavity, with the pores of the filter being sized such that particulate material in the chimney is prevented from entering the optical cavity. A similar gas permeable probe is disclosed in U.S. Pat. No. 6,064,488 in which the elongate hollow structure comprises a tube having slots relieved in the upper and lower surfaces thereof with filters of sintered metal being welded into the windows to allow gas flowing through a chimney to enter into the optical cavity. The porosity, area and location of the filters in the known arrangements determine the rate at which gas diffuses through the optical cavity. Gas permeable probes of the above kind are used in optical analyzers designed to carry out spectral analysis of gases contained in the optical cavity. Since the gases contained in the optical cavity correspond to the gases flowing through the duct or chimney it is possible, using spectral analysis, to obtain information on the types of gas that are present in the duct or chimney and their relative concentrations.

Moreover, a gas permeable probe of this kind can also be used to obtain information on various types of dust and dust contents in gas flows such as exhaust streams. This can be done if the pore size of the filter is selected such that the dust of interest can enter into and escape from the optical cavity.

Gas permeable probes of the kind to which the present application relates can be used in gas carrying ducts, especially exhaust ducts of all kinds which operate in a temperature range of e.g. 50° C. to 450° C. Such ducts are, for example, found in power stations, refuse burning plants, in cement works, in association with large furnaces, in steelworks and in gasworks.

While known gas permeable probes of the initially named kind are suitable for certain applications, they all suffer from various restrictions, so that it is difficult to use one basic type of apparatus for a variety of different measurements and applications. For example, different applications require different types of filters with different characteristics, such as pore size and hydrophobic characteristics.

Furthermore, it is frequently necessary, depending on the type of measurement that has to be carried out, to use optical windows and retroreflectors of different materials, i.e. of materials having different optical characteristics. This is however not readily possible with gas permeable probes of the known kind.

SUMMARY OF THE INVENTION

Accordingly, it is an object of the present invention to provide a gas permeable probe in which the optical window and/or the retroreflector can be readily interchanged or replaced without experiencing difficulties with the alignment of the retroreflector relative to the optical window.

It is a further object of the present invention to provide a type of modular design of a gas permeable probe which can be adapted in a relatively simple manner for use in a wide range of applications with respect to the gas temperature, gas pressure, water content, gas concentration, type of gas and with respect to the most diverse types of dust and dust contents.

At the same time, the gas permeable probe should operate reliably over a long period of time in a simple manner with a low servicing requirement and should be capable of being reliably calibrated with respect to the gases being detected while eliminating sources of error.

In order to satisfy these objects there is provided a gas permeable probe for use in an optical analyzer for an exhaust gas stream flowing through a duct or chimney, the probe comprising:

an elongate hollow structure having first and second ends and a side wall, with an optical cavity defined between the first and second ends within the side wall, a mounting structure at the first end and adapted for mounting the elongate hollow structure within the duct or chimney, a support member at the second end, a connecting structure connecting the mounting structure at the first end to the support member at the second end, an optical window at the first end permitting a beam of light originating from an optical analyzer to enter into the optical cavity to travel from the first end to the second end, a filter forming a part of the side wall, and a retroreflector provided at the second end for returning the light beam to the first end of the hollow structure, the optical window being releasably mounted at the first end of the elongate hollow structure and/or the retroreflector being releasably mounted at the second end of the elongate hollow structure.

This arrangement makes it relatively easy to change the optical window and/or the retroreflector to enable adaptation of a basic gas permeable probe to different applications. Moreover, the connecting structure connecting the mounting structure at the first end to the support member for the retroreflector at the second end ensures that the retroreflector is always correctly aligned with the optical window provided at the first end.

The retroreflector is preferably releasably connected to the support member at a side of the support member remote from the optical window and aligned with an opening in the support member. This makes it possible to remove and replace the retroreflector without having to dismantle anything other than the structure readily accessible in the immediate vicinity of the retroreflector at the second end of the elongate hollow structure.

Thus, the design makes it possible to readily exchange the retroreflector, which is mounted on the support member without it being necessary to disturb the filter.

The gas permeable probe preferably further comprises a ring recess having a base and formed in the mounting structure at the first end of the elongate hollow structure, with the optical window being disposed in the ring recess and being accessible when a filter forming part of the elongate hollow structure is removed.

Thus, the optical window can be readily exchanged after removal of the filter.

The mounting structure preferably comprises a first mounting flange at the first end of the elongate hollow structure. This first mounting flange provides a simple way of releasably mounting the optical window and the filter structure in the gas permeable probe.

In a particularly preferred arrangement the gas permeable probe further comprises a support tube connected to the first mounting flange and extending to a second mounting flange adapted for mounting to a wall of the duct or chimney. This enables the optical cavity to be mounted within the duct or chimney away from the wall of the duct or chimney, and thus in a position in which it is fully exposed to the flow through the duct or chimney, without the measurement being disadvantageously affected by boundary layer wall effects of the duct or chimney.

The ring recess is conveniently provided in the first mounting flange.

In a preferred embodiment the first mounting flange has a first side adjacent the elongate hollow structure and a second side remote from it and a pressure ring is provided at the first side. The pressure ring conveniently has a ring-shaped axial projection engaging into the ring recess in the first mounting flange.

First and second ring seals are expediently provided, with the first ring seal being disposed between the optical window and the base of the ring recess and the second seal being provided between the optical window and the axial projection of the pressure ring. This arrangement ensures satisfactory sealing at the optical window while avoiding mechanical stress in this component and thus possible damage thereto.

A plurality of threaded fasteners which extend through the pressure ring and the mounting flange are conveniently used for clamping the first mounting flange and the pressure ring together. The threaded fasteners usefully engage into a ring-shaped connecting member provided at a side of the first mounting flange remote from the pressure ring.

When the filter includes a connection flange disposed adjacent the first end of the elongate hollow structure, the threaded fasteners conveniently also pass through the connection flange. The threaded fasteners preferably engage into a ring-shaped connecting member provided at a side of the mounting flange remote from the pressure ring and the ring-shaped connecting member conveniently has an axial projection which supports a ring-shaped heater mounted thereon.

The filter preferably comprises an elongate modular filter forming part of the elongate hollow structure. The modular filter expediently has first and second opposite ends and includes a filter structure having at least one filter member, a bellows at one of the first and second opposite ends adjacent the filter structure, the connection flange at the first opposite end and a further connection flange at the second opposite end adjacent the support member. In this way the pressure ring and the optical window are removable on releasing the threaded fasteners and removing the elongate modular filter.

Although it is considered preferable to use a filter structure comprising a tube of filter material, it is also possible to use a filter structure comprising a metal tube having windows therein which are occupied by elements of filter material.

Further advantages of the invention will be set forth in the subsequent description given by way of example only with reference to the preferred embodiment as illustrated in the drawings.

BRIEF DESCRIPTION OF THE DRAWINGS

FIGS. 4 to 7 are cross-sections through the gas permeable probe of FIG. 1 taken along lines IV—IV, V—V, VI—VI and VII—VII respectively.

DESCRIPTION OF THE PREFERRED EMBODIMENTS

Figure 1:
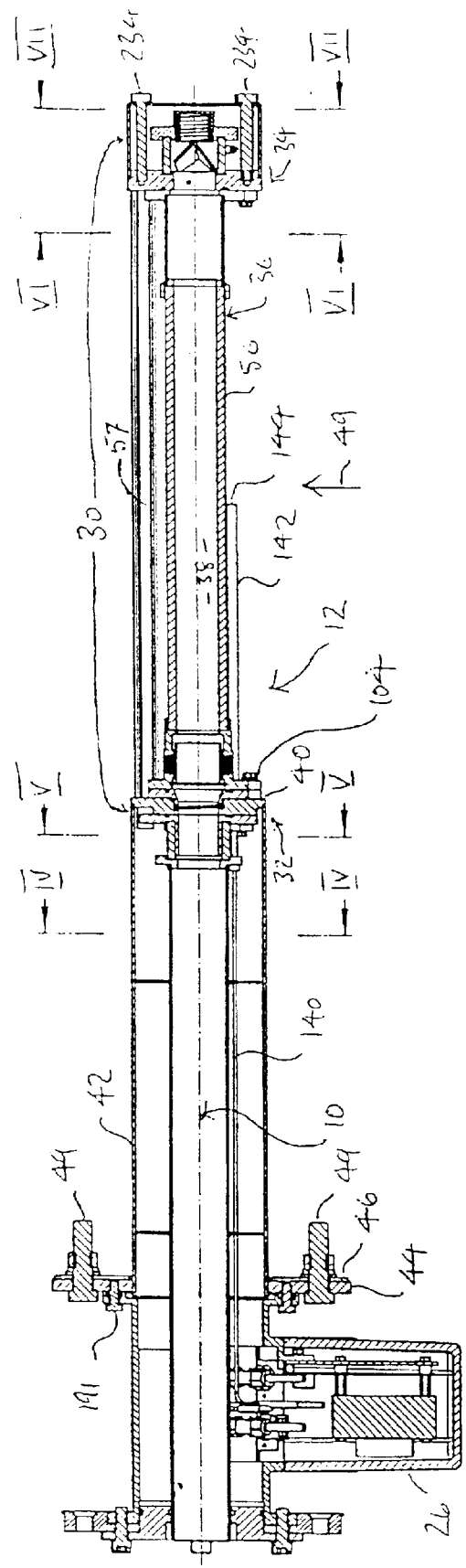
FIG. 1 shows an axially sectioned view of a gas permeable probe made in accordance with the present invention taken along lines I—I of FIGS. 4 to 7, FIGS. 1A–1C are sequential axial sections of the representation of FIG. 1 to an enlarged scale.
Figure 1A:
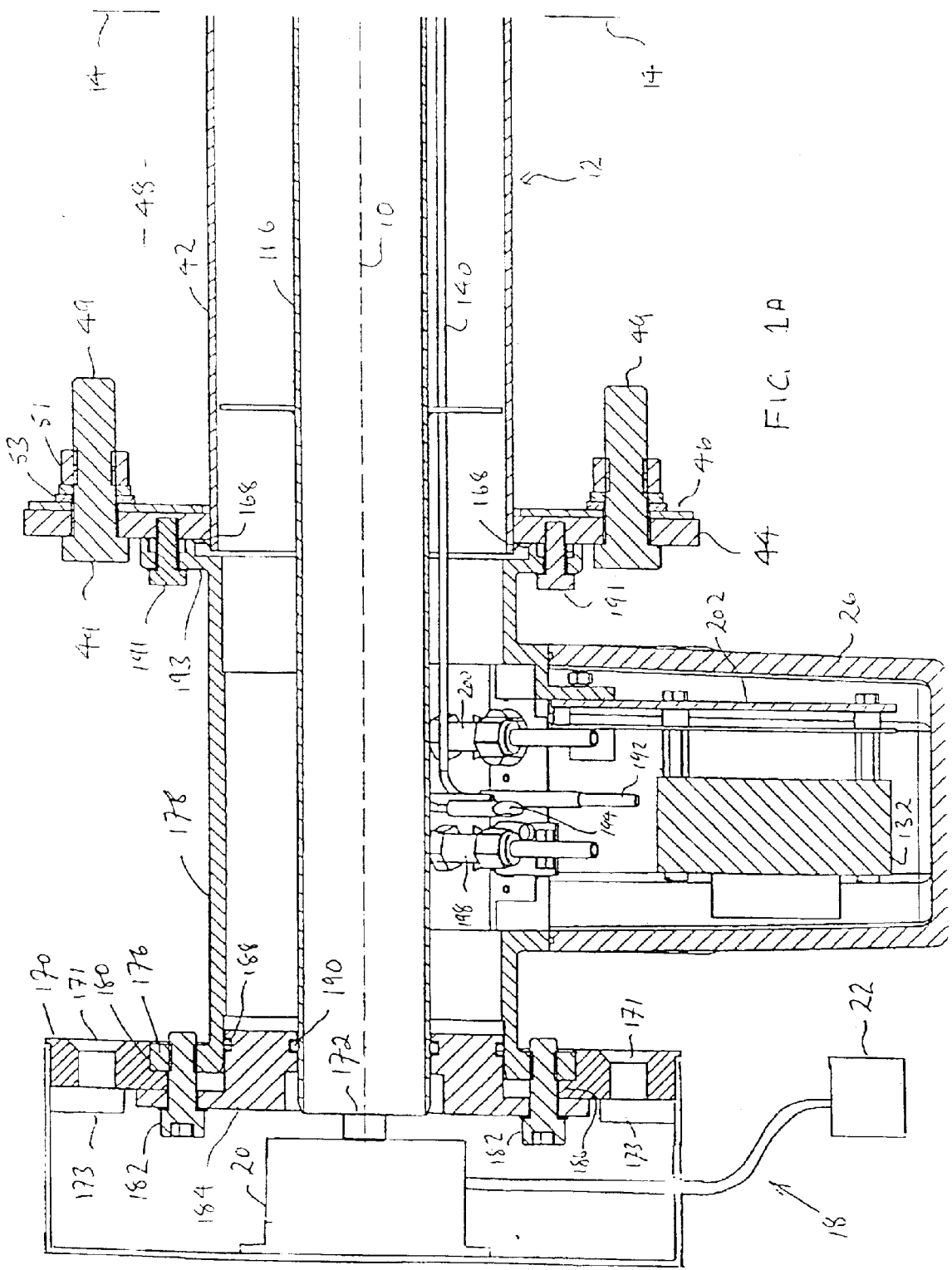
Figure 1B:
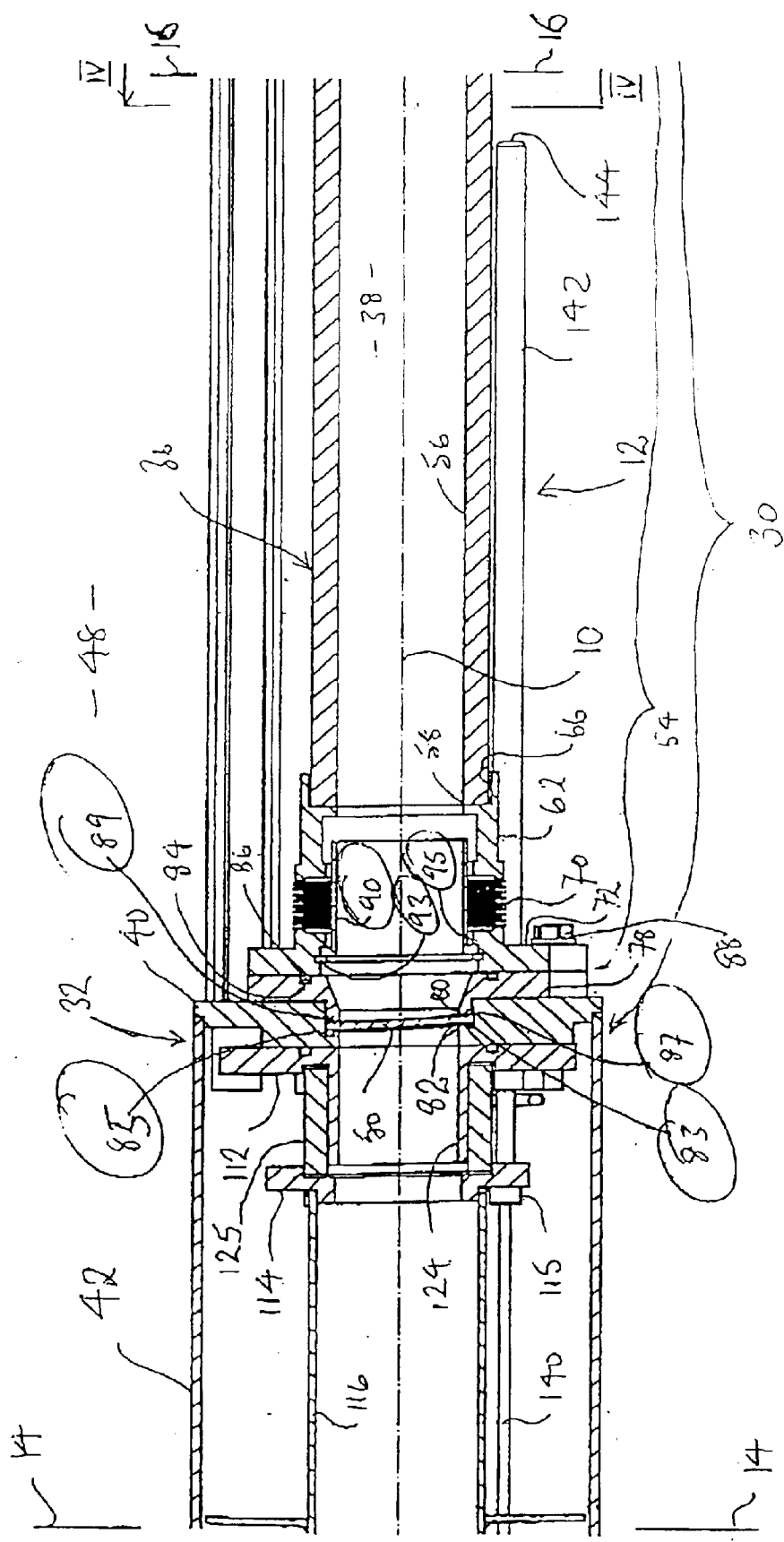
Figure 1C:
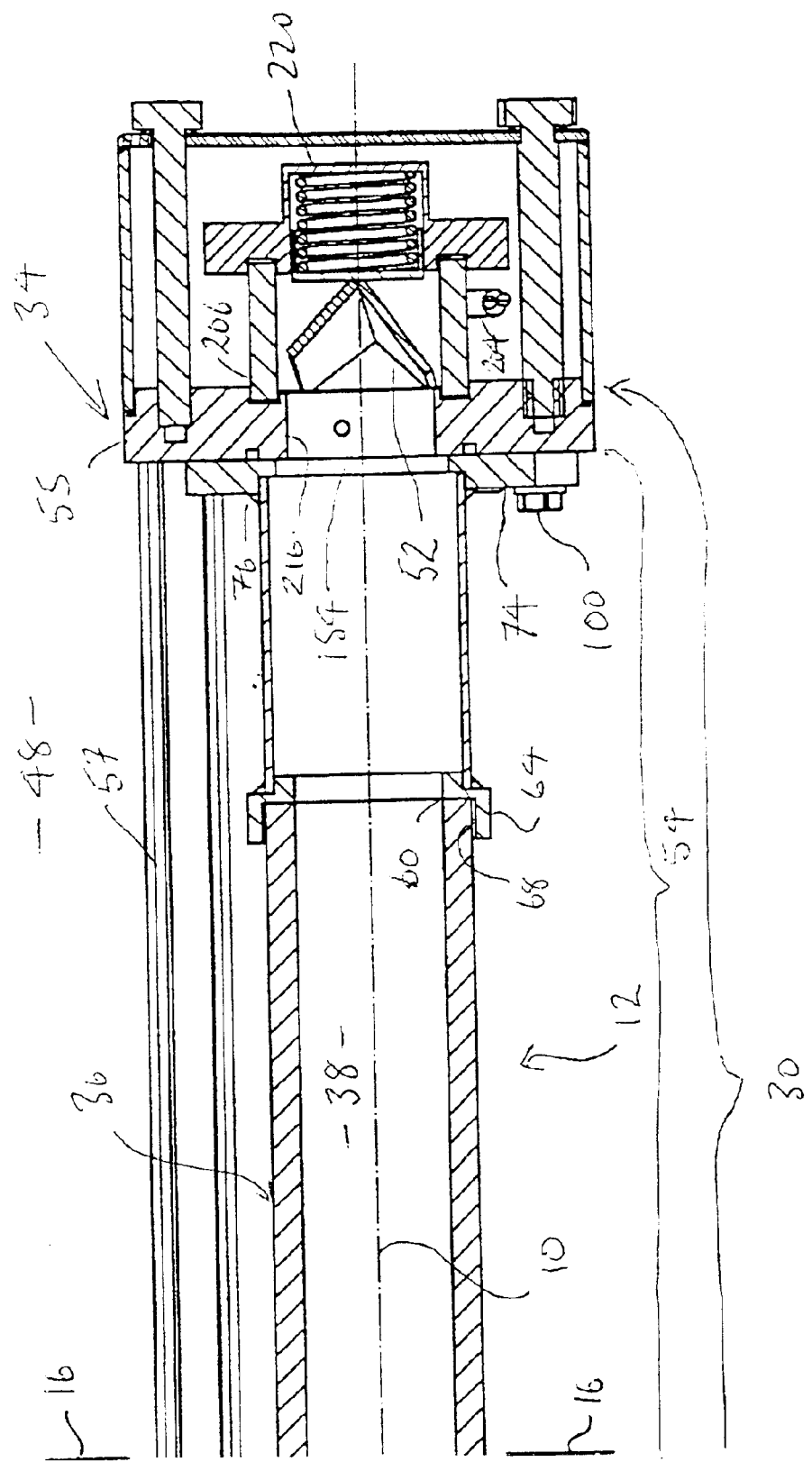

Turning first of all to FIG. 1, there can be seen an axial section along the axis 10 of a gas permeable probe indicated generally by the reference numeral 12. FIGS. 1A, 1B and 1C then show three sequential sections of the representation of FIG. 1 to an enlarged scale. The three sections of FIGS. 1A, 1B and 1C have been formed such that the position 14 at the right-hand end of FIG. 1A corresponds to the position 14 at the left-hand end of FIG. 1B and such that the position 16 at the right-hand end of FIG. 1B corresponds to the position 16 at the left-hand end of FIG. 1C.

The gas permeable probe 12 is used with an optical analyzer indicated generally by the arrow 18, which is only schematically illustrated at the left-hand end of FIG. 1A but not in FIG. 1. The optical analyzer 18 comprises a light emitter and receiver 20, a transceiver located at the left-hand end of the gas permeable probe 12 and an electrical evaluation circuit 22 which is disposed remote from the transceiver 20 in this example but which could also be combined with it. The optical analyzer includes power supplies and other items disposed within the housing 26 as will be explained later in more detail. The optical analyzer can be of any known design.

The gas permeable probe of the present invention comprises an elongate hollow structure identified generally by the reference numeral 30 in FIGS. 1B and 1C. The elongate hollow structure 30 has a first end 32 which can be seen in FIG. 1B and a second end 34 identified in FIG. 1C. The elongate hollow structure 30 has a side wall indicated generally at 36 and a hollow optical cavity 38 defined between the first and second ends 32, 34 within the side wall 36. A mounting flange 40 is provided at the first end 32 and forms part of a mounting structure including a support tube 42 and a second mounting flange 44 adapted for mounting the elongate hollow structure 30 to the wall 46 at one side of a duct 48. This connection is effected by bolts 49 which engage into nuts 51 mounted on a ring 53 fixed to the inside of the duct. A support member 55 provided at the second end 34 of the elongate hollow structure is permanently connected to the first mounting flange 40 by a connecting structure comprising two tie members 57 of which only one can be seen in FIG. 1. Both members 57 are shown in FIG. 6.

The gas permeable probe is thus arranged in the duct 48 for carrying out measurements on a gas stream flowing through the duct in the general direction of the arrow 49. An optical window 50 is provided at the first end 32 of the elongate hollow structure 30 and permits a beam of light (not shown) originating from the transceiver 20 to enter into the optical cavity 38 to travel in a direction generally along the longitudinal axis 10 from the first end 32 to the retroreflector 52 provided at the second end 34 of the elongate hollow structure on the support member 55. The elongate hollow structure includes a filter structure identified generally by the reference numeral 54 which includes, in this embodiment, a tube 56 of filter material having first and second ends 58, 60. The end 58 of the tube 56 of filter material is connected, for example by brazing, to a filter mounting tube 62, and the second end of the tube 56 of filter material is connected to a filter support tube 64. This connection can again be effected by brazing. The tube 56 of filter material can either be a filter of sintered metal or a filter of ceramic material and in either case it is possible to find a braze which is suitable for connecting the two ends 58 and 60 of the tube of filter material to the metallic filter mounting tube 62 and to the metallic filter support tube 64.

Alternatively, these connections can be formed as screw connections, or as adhesively bonded connections, or as interference connections. Irrespective of the type of connection used, it is convenient for the respective first and second ends 58 and 60 of the tube of filter material 56 to be received in ring recesses 66 and 68 provided in the right-hand end of the filter mounting tube 62 and in the left-hand end of the filter support tube 64 respectively.

The left-hand end of the filter mounting tube 62 in FIG. 1B is connected via a flexible metal bellows 70 to a connection flange 72 at the left-hand end of the tubular filter structure 54 in FIG. 1B, and a similar connection flange 74 is provided at the right-hand end of the filter support tube 64 in FIG. 1C. The flexible metallic bellows 70 is connected at its two axial ends to the metallic connection flange 72 and to the filter mounting tube 62 by welding or brazing and the filter support tube 64 is connected to the connection flange 74 by a welded joint indicated in the usual way by a triangular fillet 76 in FIG. 1C. The connection flanges 72 and 74 are both of generally rectangular shape with rounded ends, as can be seen from FIG. 6 for the connection flange 74.

Disposed between the connection flange 72 and the mounting flange 40 is a pressure ring 78 which has a ring-like projection 80 for trapping the optical window 50 between itself and the base of a ring recess 82 provided at the mounting flange 40. A ring groove 84 is provided in the right-hand end face of the pressure ring 78 and accommodates a graphite seal 86 which is compressed when the assembly is bolted together by bolts, such as 88, as can be seen from FIG. 2. A resilient ring seal 83 is provided in a ring groove 85 at the base of the ring recess 82 between the optical window 50 and the ring recess 82. A second ring seal 87 is provided between the ring projection 80 and the optical window 50, in a ring groove 89 in the ring projection 80.

These resilient ring seals 83, 87 ensure that the optical window 50 is sealed with respect to both the mounting flange 40 and with respect to the pressure ring 78 and thus with respect to the elongate hollow structure 54. At the same time they ensure that the optical window 50 is not damaged by mechanical pressure exerted between the pressure ring 78 and the mounting flange 40. A graphite seal is provided in a ring groove 79 in the pressure ring 78 to effect a seal between the pressure ring and the connection flange 72.

Within the connecting flange 72 and the flexible metallic bellows 70 there is located a sleeve 90. The sleeve 90 is only located at one end 91, between a circlip 93 and a ring shoulder 95, in order that differential thermal expansion and contraction and resilient deflection of the bellows can take place without this affecting the sleeve.

It will be noted from FIGS. 1B and 1C in conjunction with FIG. 6 that the filter module assembly 54 comprising the connection flange 72, the flexible bellows 70, the filter mounting tube 62, the tube of filter material 56, the filter support tube 64 and the connecting flange 74 can be removed from the gas permeable probe by releasing the screws 88 and also the further screws 100 provided at the second end of the elongate hollow structure, which connect the flange 74 to the support member 55. Following the release of the screws 88 and 100 the filter module 54 can be slid sideways, i.e. at right angles to the axial direction 10 out of the assembly, as indicated by the arrow 102 in FIG. 6. The reference numerals 104 and 106 refer to radial slots provided in the connecting flange 72 and in the connecting flange 74 which allow the flange to be passed over a tube 142 which serves for the orientation of the filter module assembly 54 when it is inserted and acts as a stop to ensure it is correctly positioned. At the left-hand side of the mounting flange 40 in FIGS. 1B and 2 there is provided a connecting member 112 which serves for the connection to a mating flange 114 provided at the right-hand end of an inner tube 116 provided coaxially within the support tube 42. This connection is effected by three bolts 115 of which only one is shown in FIGS. 1 and 1B, but which can all be seen in FIG. 5.

The connecting member 112 has an axially projecting sleeve portion 124 which serves to carry a ring-like heater 125 mounted on it and trapped between it and the mating flange 114. The ring-like heater 125 is connected via leads (not shown) to a terminal block 126 provided within the support tube 42 on the mating flange 114, as can be seen from the sectioned drawing of FIG. 2. The terminal block 126 is connected via an electrical lead 128 enclosed within a protective tube 130 extending in the space between the support tube 42 and the inner tube 116 to the power supply 132 provided in the housing 26 shown in FIG. 1A. The purpose of the ring-like heater 124 is to heat the optical window 50, so that at low operating temperatures and with moist gases in the duct or chimney 48 condensation at the optical window 50 is avoided. For this purpose, the temperature of the optical window 50 is held at a temperature above that of the local environment.

Figure 2:
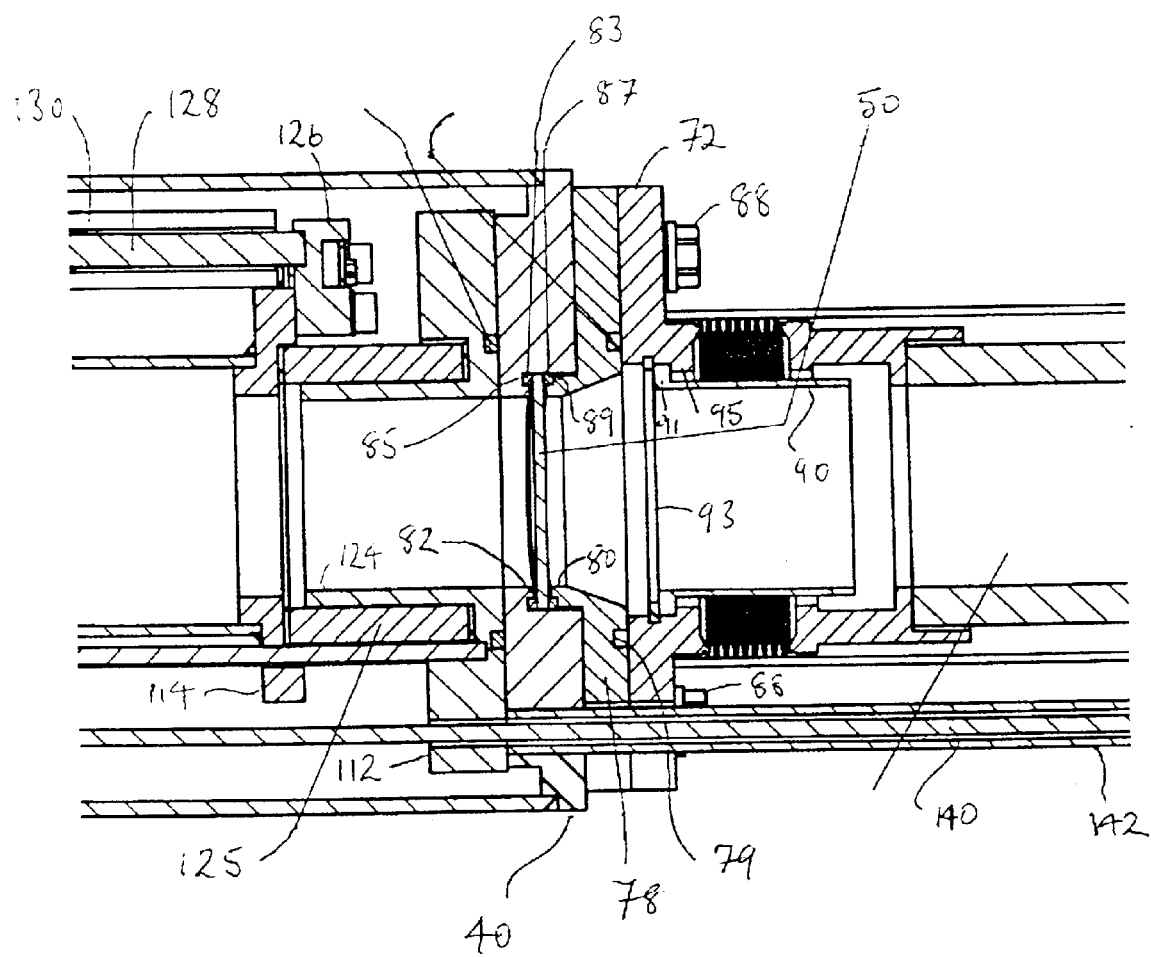
FIG. 2 is a section on an enlarged scale of the gas permeable probe of the invention in the region of the optical window and the bellows at an orientation around the longitudinal axis corresponding to the section plane II—II of FIG. 6.

Referring also to FIGS. 1A, 1B and 2, the reference numeral 140 refers to a thermocouple lead which extends in the inner space between the support tube 42 and the inner tube 116 and enters into a protective metallic tube 142 shown in FIG. 1B which terminates at a thermocouple 144 at the right-hand end of FIG. 1B. The thermocouple 144 thus measures the temperature in the duct 48 directly adjacent the surface of the tube of filter material 56 and this temperature can be considered substantially equal to the temperature prevailing in the optical cavity 38. Although not shown in FIGS. 1A and 1B, this tube 142 can also extend through the intermediate space 144 between the support tube 42 and the inner tube 116.

It can also be seen from FIG. 1A that the support tube 42, which is welded to the second mounting flange 44 at the fillet weld 168, terminates essentially at the second mounting flange 44, whereas the inner tube 116 is extended beyond the second mounting flange 44 to a third mounting flange 170 provided at the left-hand end of FIG. 1A. This third mounting flange 170 serves for the attachment of transceiver 20 to the apparatus. This is achieved by screws (not shown) which extend through countersunk bores 171 in the third mounting flange into bores provided in lugs 173 of the transceiver housing. The left-hand end of the inner tube 116 terminates at a window member 172 which does not affect, or at least substantially does not affect, light of the wavelength or wavelengths used for the spectral analysis.

It will be noted that the third mounting flange 170 is connected to a connection flange 176 at the end of a carrier tube 178, which engages into a ring recess 180 in the third mounting flange 170. This connection is effected by means of bolts 182 which pass through a disc member 184 shaped to trap a radially inwardly projecting flange 186 of the third mounting flange 170 between itself and the connection flange 176. The disc member 184 has two O-rings 188, 190 in order to seal the joint between itself and the carrier tube 178 and between itself and the inner tube 116 while permitting relative thermal expansion between the components, which can be taken up by axial sliding between the ring seal 188 and the carrier tube 178 and between the ring seal 190 and the inner tube 116.

The carrier tube 178 is in turn bolted to the second mounting flange 44 by bolts 191 extending through a further connection flange 193 into the second mounting flange. In addition to containing the power supply 132, the housing 26 also contains a connection 192 to the lead 140 leading to the thermocouple 144, a connection 194 to a second thermocouple lead 196, as well as a connection 198 to a pressure transducer provided in the optical cavity and a connection 200 for a tube or line 201 (FIG. 6) for supplying gas to the optical cavity. Since the connection to the line for supplying gas to the optical cavity can be used to supply either a calibration gas, or a neutral gas, or a gas used to purge the optical cavity and to clean particulate material from the outside of the tube 56 of filter material, valves (not shown) are provided which allow the respective gases to be admitted to the line 201 as required and which also permit the tube to be isolated relative to the material of the housing, so as to prevent flue gases entering into the housing when no gases are being supplied to the optical cavity via the line 201.

In addition to these items, the housing conveniently contains a circuit board 202 having circuits (not shown) mounted thereon for regulating the supply of electrical energy via the line 128 to the ring heater 125 associated with the optical window 50 and via a line 204 (not shown in FIG. 1A but in FIGS. 1C, 3, 4, 5, 6 and 7) to the similar ring heater 206 associated with the retroreflector 52. These regulating circuits are designed to regulate the supply of electrical energy to the respective ring heaters 125, 206, taking into account the temperature prevailing in the duct, as measured by the thermocouple 144, and thus taking into account the cooling or heating effect of the gases passing through the duct, so as to maintain temperatures of the optical window and of the retroreflector, which can be preset temperatures, sufficient to ensure condensation does not occur.

Figure 3:
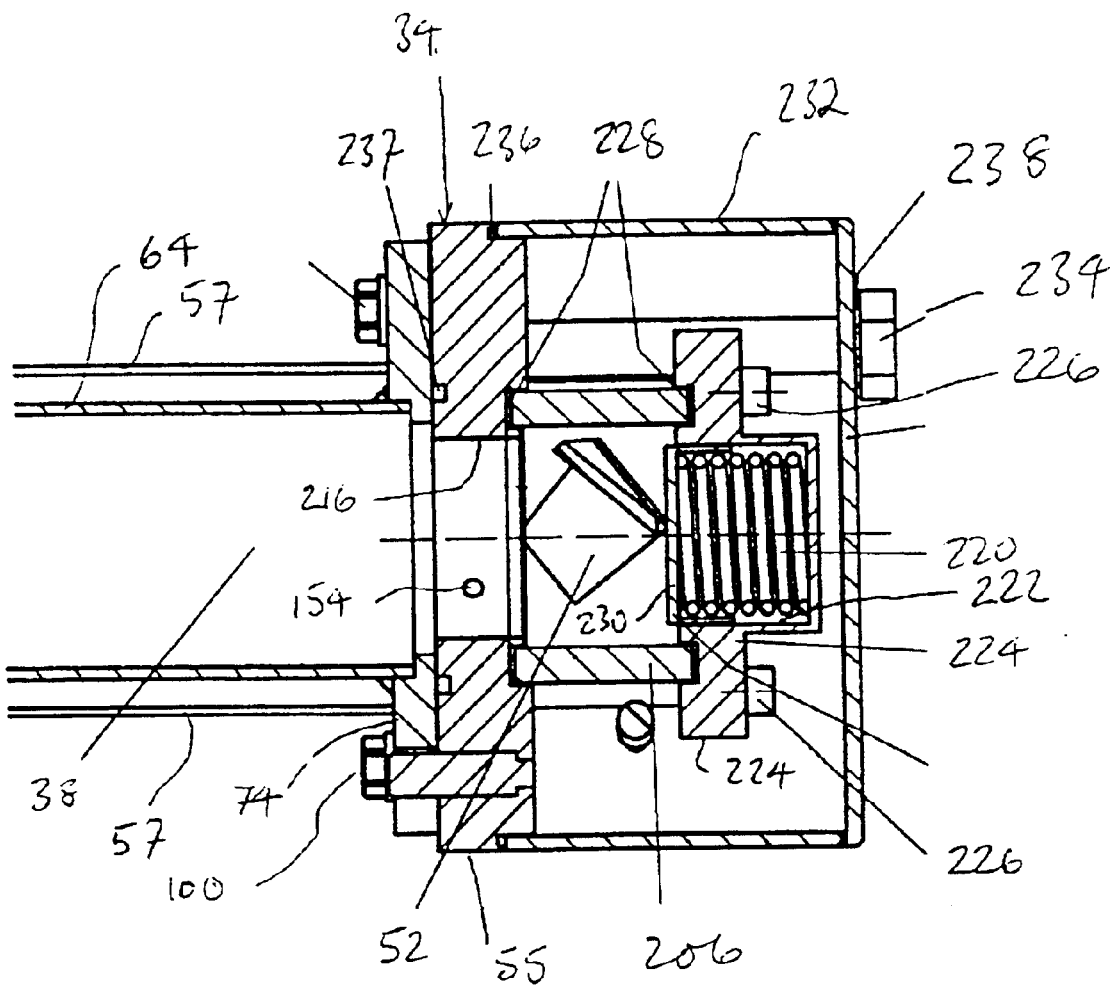
FIG. 3 is an enlarged section corresponding to FIG. 1C and shows the region of the retroreflector.

Turning now to FIGS. 1C and 3, the retroreflector arrangement at the second end 34 of the elongate hollow structure will now be described in more detail. As already mentioned, the connection flange 74 at the right-hand end of the filter support tube 64 is secured by screws 100 to the support member or flange 55, which is in turn connected via the tie members 57 to the first mounting flange 40 at the left-hand end 32 of the elongate hollow structure. As indicated in FIG. 6, the tie members 57 each have the form of an arcuate metal plate 61 with two tubes 63 and a stiffener 65 welded to it. The modular filter unit 54 can be inserted and removed through the spaces between the tie members 57 as indicated by the arrow 102. The tubes 201, 210 for the calibration gas and for the pressure sensor extend through respective ones of the tubes 63, as does the electrical lead 204 for the heater 206 associated with the retroreflector 52. This can be seen from the reference numerals 201, 210 and 204 entered in FIG. 6. The tube 201 for the calibration gas, which is also used for the neutral gas and the filter cleaning gas flow, opens via a passage 154 in the support member 55 and the orifice 154 into the optical cavity.

The support member 55 has a central opening 216 and acts at its end face 218 adjacent the central opening as a support for the open end of the retroreflector 52 which is formed in this embodiment as a corner reflector or triple reflector. If desired, a window can be provided in front of the retroreflector. The retroreflector is urged against the end face of the plate member by a compression coil spring 220 received in a pot-like recess 222 of a pressure disc or reaction member 224 which is spaced from the plate member by the ring heater 206. Three bolts 226, of which two can be seen in FIG. 3, serve to connect the pressure disc to the support member 55, with the ring heater 206 acting as a spacer. Seals 228 are provided at the two axial ends of the ring heater 206 to ensure that a sealed arrangement is present. The compression coil spring acts on the retroreflector via a cup member or piston 230 which serves to distribute the load from the spring 220 on the retroreflector. The compression coil spring 220 is a resilient member which takes into account differential thermal expansion between the retroreflector 52 and the structure 55, 206, 224, 226 surrounding it. The arrangement comprising the retroreflector, the pressure disc and the coil spring and cup member is surrounded by an outer cover 232 which is secured to the plate member via two screws 234. This cover 232, provided with seals at 236 and 238, isolates the retroreflector assembly from the gases passing through the duct 48. A further graphite seal 237 is provided between the connection flange 74 and the support member 55 in a ring groove formed in the support member.

The entire gas permeable probe can be removed as a module from the duct or chimney by releasing the bolts 49. In addition, the module comprising the transceiver 20, the housing 26, the carrier tube 178, the ring plate 184 and the third mounting flange 170 can be removed from the modular assembly comprising the second mounting flange 44, the support tube 42, the inner tube 116 and the elongate hollow structure 30 by releasing the bolts 191.

The filter module 54 comprising the connection flange 72, the flexible metallic bellows 70, the filter mounting tube 62, the filter tube member 56, the filter support tube 64 and the connection flange 74 can be removed as a unit from the gas permeable probe by releasing the screws 88 and 100 without disturbing the remainder of the assembly. Once the filter module has been removed, the pressure ring 78 can also be withdrawn axially from the first mounting flange 40 and the optical window 50 can be readily removed and exchanged as can the ring seals 83 and 87.

In addition, the module formed by the retroreflector assembly can easily be dismantled by removing the screws 234 connecting the cover 232 to the plate member and subsequently removing the screws connecting the pressure disc 224 to the support member 55 so that the retroreflector 52 and/or the ring heater 206 and the seals 228 associated therewith can be removed and replaced as necessary. The module comprising the support member 55 and the connection structure 57 as well as the first mounting plate 40 forms a welded structure which remains together as a module.

The cover of the housing 26 can be removed whenever required, thus providing access to the power supply 132 and to the other items contained in the housing.

Because the inner tube 10 is sealed in use by the optical windows 172 and 50, there is no danger of it becoming contaminated internally, and therefore there is no danger of contamination having an unpredictable effect on the light used for the spectral analysis. The conduction of the sensor line 140, the pressure sensing line 210 and the gas conducting line 201 as well as the electrical leads 128, 204 within the intermediate space between the support tube 42 and the inner tube 116 ensures that substances evaporating from these components at the elevated temperatures prevailing within the duct or chimney 48 do not contaminate the optical cavity or the interior of the inner tube 116 and therefore can also not affect the quality of the spectral analysis.

The gas permeable probe of the present invention has the following advantages and features which are united in the modular design:

A large optical absorption path.

The design permits absorption paths of 1 m for the standard design and can be made longer or shorter depending on the requirements by substituting connection structures and filter structures of different lengths which are available as exchange modules.

Integrated temperature measurement for the gas temperature.

The measurement sensor is positioned in the exhaust gases flowing through the duct or chimney and is thus protected against any corrosive substances present in the flue gases. Because of its close proximity to the filter structure, the temperature measurement is representative of the temperature prevailing in the flue or duct at the filter structure and thus in the optical cavity. Alternatively, it is also possible to place the temperature measuring sensor in the optical cavity. However, the provision of the temperature measuring sensor outside of the optical cavity facilitates the modular construction and the exchange of the filter module.

Integrated pressure measurement of the pressure in the duct or chimney.

The pressure of gas is measured in the measuring cavity and serves for the normalization of the measurement results, especially when calibration measurements are being carried out, since then the calibration gas flowing into the cavity can be set with a higher pressure and this higher pressure must be known for the correct determination of the calibration gas values.

Gas checking is possible.

The analyzers used with the gas permeable probe and the gas permeable probe can be checked with respect to their measurement functions by using calibration gases and neutral gases to ensure that they are functioning correctly. The gas examination can take place manually or automatically. The optical cavity can be used as a neutral path by blowing the volume of the optical measurement path free of other gases using air or $N_2$. This can take place at any time, the gas permeable probe does not need to be removed for this purpose, and the apparatus remains at its point of installation.

Use in pressurized systems is possible.

Since the optical measurement cavity is closed at one end by the optical window and at the other end by a retroreflector assembly, it can be designed for operation at elevated pressure, such as for example 2 bar. It is, however, necessary to ensure that the optical analyzer is calibrated for such pressures.

No NBR problems (Null-Punkt Reflektor=zero point reflector).

This advantage is achieved because the optical measurement path can be blown free of gases and thus filled with a neutral gas so that the zero point can be detected using the optical cavity filled with the neutral gas. It is thus possible to dispense with a separate zero point reflector. All the optical boundary surfaces which participate in the formation of the measured value are thus also involved in the zero point measurement and it is no longer possible for the measured values to be influenced by drifting of the zero point measurement.

Elimination of the sensitivity to dust.

Since dust can be separated out at the surface of the filter material it no longer affects the quality of the measurement, unless the measurement is intended to detect dust particles, in which case the pore size of the filter is selected to enable the dust particles of interest to enter the optical cavity.

It can be used at high dust concentrations.

The filters in the gas permeable probe can be designed to reliably keep dust out of the optical measurement cavity (by selection of the pore size of the filter) so that it can be ensured that dust does not influence the measurement result.

No specially routed flushing air system is required.

Since dust is essentially deposited on the filter it does not reach the optical boundary surfaces. Because no permanent flushing air supply is required, there is also no possibility of the flushing air giving rise to problems, in particular with small ducts.

No problem with external light sources.

Because the beam path used for the measurement is fully encapsulated, no external light can enter into the beam path.

Utilize action with unfavorable flow conditions.

The gas permeable probe can be used, when turbulence is present and at very low gas speeds.

It can be used with pressures which change significantly. Because no flushing air is required, the gas permeable probe cannot be affected by flushing air. In conventional systems, which require flushing air, the flushing air supply must be laid out for the maximum operating pressure, and at lower operating pressures flushing air affects the measurement.

It can be used with high moisture contents.

By utilizing filter structures with a hydrophobic membrane and small pore sizes around 0.2 $\mu$m, water droplets can be kept out of the optical cavity. Only gaseous water enters into the measurement cavity and this at small time constants.

Matching of the optical absorption path to the gas concentration to be measured.

The length of the measurement cavity can be matched to the gas concentration to be measured, at low concentrations along the absorption paths that are required. At high concentrations shorter absorption paths are sufficient.

Exchange of the optical components in accordance with the required spectral range (ultraviolet to infrared).

The optical components that are required, that is, the windows and the retroreflector, can be matched to the required spectral range by choosing suitable materials and surfaces of the components.

Crossed beam path for laser applications.

When used with a laser spectrometer the beam path in the measurement cavity is crossed. This beam guidance prevents interference effects.

Supply of calibration gases.
Calibration gases and neutral gases can be connected to gas connecting fittings and directed into the optical cavity through gas conducting lines.

Calibration gas heating.
The gas conducting line is laid out so that the calibration gas or neutral gas is heated up to the temperature of the gas flow through the duct. The line leading into the optical cavity has direct contact to the exhaust gas in the duct. A body is preferably inserted into the gas conducting line which continually swirls the air (for example a bar with a spiral spring placed around it can be disposed inside the gas conducting line) and in this way the best possible contact of the gas molecules with the outer wall of the gas conducting line can be ensured. In this manner, the gas is heated up approximately to the gas temperature prevailing within the duct and the cross-section of the line can be designed such that a pressure pulse can also be effectively transmitted in order to free the outer surface of the filter from dust deposits. The gas conducting line can be the same line which serves to introduce calibration gases or neutral gases into the optical cavity or it can be a separate dedicated line.

Ceramic filters with inert behavior can be used which have no catalytic effect on the gases to be measured.

Ceramic filters can also be used with coatings of a PTFE material in order to repel liquid water while being simultaneously permeable to gas.

Compensation for different coefficients of expansion.
This is achieved, as explained, by the use of the membrane bellows which, for example, can take account of the differential thermal expansion between the ceramic filter material and the stainless steel of the connecting structure.

Temperature range.
The temperature range can be up to and beyond 450° C. for dry applications. The temperature range can be at least up to 200° C. for wet applications. The maximum possible temperature at which the hydrophobic coating, for example the PTFE membrane, can be used is limited by the operating limit of PTFE and by the available seal materials.

Heatable optical boundary surfaces.
The use of heating for the optical boundary surfaces makes it possible to prevent such misting up when the gas permeable probe is used, with intermittent operation, and at measurements close to the dew point. The optical boundary surfaces are heated to a temperature which is 55° C. higher than the local environment. From temperatures above 160° C. onwards, the heating can be switched off.

Separation of the constructional space for the guidance of leads and the optical beam path.
This separation makes it possible to avoid disturbing effects caused by foreign components. Thus contaminants on components and substances which are given off by the components are kept away from the optical cavity, so that they cannot affect the measurements.

A minimum number of seal locations relative to the medium flowing through the duct or chimney.
Because only a few seal positions are present the chances of leakage are minimized.

Integrated electronics for temperature and pressure measurement and for the monitoring of the operation of the gas permeable probe.

Integrated regulation system for the heating of the optical boundary surfaces with monitoring of their operation by means of current measurements.

Output of the measurement data and input of parameters for the gas permeable probe and measurement system via a field bus.

What is claimed is:

1. A gas permeable probe for use in an optical analyzer for an exhaust gas stream flowing through a duct or chimney, the probe comprising:
    an elongate hollow structure having a length and including first and second ends and a side wall, with an optical cavity defined between said first and second ends within said side wall,
    a mounting structure at said first end and adapted for mounting said elongate hollow structure within said duct or chimney,
    a support member at said second end,
    a connecting structure connecting said mounting structure at said first end to said support member at said second end,
    an optical window at said first end permitting a beam of light originating from an optical analyzer to enter into said optical cavity to travel from said first end to said second end,
    a filter module having a filter forming a part of said side wall, said filter module being removable from said connecting structure in a direction transverse to the length of the elongate hollow structure, and
    a retroreflector provided at said second end for returning said light beam to said first end of said hollow structure and being releasably connected to said support member,
    said optical window being releasably mounted at said first end of said elongate hollow structure between said mounting structure and said filter module, there being a first heater associated with said optical window and a second heater associated with said retroreflector.

2. A gas permeable probe in accordance with claim 1, wherein said retroreflector is releasably connected to said support member at a side of said support member remote from said optical window and aligned with an opening in said support member.

3. A gas permeable probe in accordance with claim 2 and further comprising a releasable cover member surrounding said retroreflector.

4. A gas permeable probe in accordance with claim 3, including at least one threaded fastener releasably connecting said cover member to said support member.

5. A gas permeable probe in accordance with claim 2, said retroreflector having a front side disposed adjacent said support member and a rear side disposed remote from said support member, a releasable reaction member spaced from said support member and one spring resiliently mounting said retroreflector with respect to one of said support member and said reaction member.

6. A gas permeable probe in accordance with claim 5, said one spring being disposed between said releasable reaction member and said rear side of said retroreflector, said front side of said retroreflector being disposed adjacent said support member.

7. A gas permeable probe in accordance with claim 5, said one spring being disposed between said support member and said front side of said retroreflector, said rear side of said retroreflector being disposed adjacent said reaction member.

8. A gas permeable probe in accordance with claim 5, wherein said reaction member has a central recess and said one spring is disposed in said central recess.

9. A gas permeable probe in accordance with claim 8, wherein said one spring comprises a compression coil spring.

10. A gas permeable probe in accordance with claim 9, including a movable piston between said compression coil spring and said rear side of said retroreflector, said piston being movably guided in said recess.

11. A gas permeable probe in accordance with claim 5, including at least one threaded fastener for connecting said reaction member to said support member.

12. A gas permeable probe in accordance with claim 5, wherein said reaction member is rigidly connected to said support member via a spacer.

13. A gas permeable probe in accordance with claim 12, wherein said spacer is a cylindrical spacer separate from said reaction member having first and second ends.

14. A gas permeable probe in accordance with claim 13, wherein said cylindrical spacer is formed as an electrical heater for said retroreflector.

15. A gas permeable probe in accordance with claim 13, including first and second ring seals at said first and second ends of said spacer.

16. A gas permeable probe in accordance with claim 13, wherein said first and second ends of said spacer are received in respective ring recesses in said support member and said reaction member.

17. A gas permeable probe in accordance with claim 1 and further comprising a ring recess having a base and formed in said mounting structure at said first end of said elongate hollow structure, said optical window being disposed in said ring recess and being accessible when a filter forming part of said elongate hollow structure is removed.

18. A gas permeable probe in accordance with claim 17, wherein said ring recess is provided in a first mounting flange of said mounting structure.

19. A gas permeable probe in accordance with claim 18, wherein said mounting flange has a first side adjacent and a second side remote from said elongate hollow structure, and including a pressure ring at said first side.

20. A gas permeable probe in accordance with claim 19, wherein said pressure ring has a ring-shaped axial projection engaging said ring recess.

21. A gas permeable probe in accordance with claim 20, wherein first and second ring seals are provided, said first ring seal being disposed between said optical window and said base of said ring recess and said second seal being provided between said optical window and said axial projection of said pressure ring.

22. A gas permeable probe in accordance with claim 21, including a ring groove at said base of said recess and a ring groove in said axial projection, said first and second ring seals each being arranged in a respective one of said ring grooves.

23. A gas permeable probe in accordance with claim 19 and further comprising:
a plurality of threaded fasteners extending through said pressure ring and said mounting flange for clamping them together.

24. A gas permeable probe in accordance with claim 23, wherein said threaded fasteners engage a ring-shaped connecting member provided at a side of said mounting flange remote from said pressure ring.

25. A gas permeable probe in accordance with claim 23, wherein said filter includes a connection flange disposed adjacent said first end of said elongate hollow structure and said threaded fasteners pass through said connection flange.

26. A gas permeable probe in accordance with claim 23, including a heater for said optical window positioned adjacent said optical window.

27. A gas permeable probe in accordance with claim 26, wherein said threaded fasteners engage a ring-shaped connecting member provided at a side of said mounting flange remote from said pressure ring, said ring-shaped connecting member having an axial projection and said heater comprising a ring-shaped heater mounted on said axial projection of said ring-shaped connecting member.

28. A gas permeable probe in accordance with claim 25, wherein said filter comprises an elongate modular filter forming part of said elongate hollow structure, said modular filter having first and second opposite ends and including a filter structure having at least one filter member, a bellows at one of said first and second opposite ends adjacent said filter structure, said connection flange at said first opposite end and a further connection flange at said second opposite end being adjacent said support member, said pressure ring and said optical window being removable on releasing said threaded fasteners and removing said elongate modular filter.

29. A gas permeable probe for use in an optical analyzer for an exhaust gas stream flowing through a duct or chimney, the probe comprising:
an elongate hollow structure having first and second ends and a side wall, with an optical cavity defined between said first and second ends within said side wall,
a mounting structure at said first end and adapted for mounting said elongate hollow structure within said duct or chimney,
a support member at said second end,
a connecting structure connecting said mounting structure at said first end to said support member at said second end,
an optical window at said first end permitting a beam of light originating from an optical analyzer to enter into said optical cavity to travel from said first end to said second end,
a filter module defining a part of said side wall, said filter module comprising a connection flange for connection to said mounting structure, a flexible metallic bellows, a filter tube member and a connection flange for mounting said filter tube member to said support member, said filter module being removable sideways from and relative to said connecting structure, and
a retroreflector provided at said second end for returning said light beam to said first end of said hollow structure and being releasably connected to said support member at a side of said support member remote from said support member, said support member having an opening and said retroreflector being aligned with said opening,
said optical window being releasably mounted at said first end of said elongate hollow structure between said mounting structure and said filter module, there being a first heater associated with said optical window and a second heater associated with said retroreflector.

30. A gas permeable probe in accordance with claim 29, said filter member having first and second ends and said filter module further including a filter mounting tube disposed at and connected to said first end of said filter member and a filter support tube disposed at said second end of said filter member and connected to said connecting flange for mounting said filter module to said support member.

31. A gas permeable probe in accordance with claim 30, said bellows having first and second ends, said first end of said bellows being connected to said connection flange for connection to said mounting structure and said second end of said bellows being connected to said filter mounting tube.

32. A gas permeable probe in accordance with claim 31, there being a sleeve located within said bellows and connected at one end to said connecting flange for connecting said filter module to said mounting structure.

33. A gas permeable probe in accordance with claim 29, said optical window being disposed between said mounting structure and a pressure ring disposed adjacent said connecting flange for connecting said filter module to said mounting structure.

* * * * *